United States Patent [19]
Corbin

[11] Patent Number: 5,129,255
[45] Date of Patent: Jul. 14, 1992

[54] PHOTOACOUSTIC DETECTION AND TRACKING APPARATUS

[75] Inventor: Robert L. Corbin, Long Beach, Calif.

[73] Assignee: The Aerospace Corporation, El Segundo, Calif.

[21] Appl. No.: 418,044

[22] Filed: Oct. 6, 1989

[51] Int. Cl.$^5$ .................................. G01N 29/02
[52] U.S. Cl. .................................. 73/24.02
[58] Field of Search .................... 73/24, 24.02

[56] References Cited

U.S. PATENT DOCUMENTS

| | | | |
|---|---|---|---|
| 3,938,365 | 2/1976 | Dewey, Jr. | 73/24 |
| 3,948,345 | 4/1976 | Rosencwaig | 73/24 X |
| 4,163,382 | 8/1979 | Amer | 73/24 |
| 4,200,399 | 4/1980 | Kimble et al. | 73/24 X |
| 4,457,162 | 7/1984 | Rush et al. | 73/24 X |
| 4,594,004 | 6/1986 | Ishida et al. | 73/24 X |
| 4,622,845 | 11/1986 | Ryan et al. | 73/24 |
| 4,817,413 | 4/1989 | Asano et al. | 73/24 |

Primary Examiner—Hezron E. Williams
Assistant Examiner—Joseph W. Roskos
Attorney, Agent, or Firm—William J. Burke

[57] ABSTRACT

An electronic system for detecting and tracking the resonant frequency of a photoacoustic cell is described. The system includes and makes use of inherent signal acquisition properties. The detection and tracking circuitry promotes acoustic oscillation at the cell resonant frequency while the amplitude of the acoustic oscillation is automatically controlled at a specific reference level. Under normal operation, a change in system oscillation amplitude with respect to the reference level is considered to be the result of additional acoustic excitation other than that provided by the electronic system. Changes in the oscillation amplitude, as compared to a reference level, produce an error signal which is directly related to the additional acoustic excitation. The system is particularly useful in measuring gaseous phase materials over a wide dynamic range of concentrations.

2 Claims, 3 Drawing Sheets

PHOTOACOUSTIC DETECTION AND TRACKING APPARATUS

The invention described herein may be manufactured and used by or for the Government of the United States for governmental purposes without the payment of royalty therefor.

BACKGROUND OF THE INVENTION

1. Field of the Invention

The present invention relates to an electronic system for detecting, tracking and maintaining a particular frequency. Specifically, the invention is used to detect and track acoustic resonance frequencies for use in conjunction with a photoacoustic spectroscopy apparatus.

2. Description of the Prior Art

It is well known that a tunable laser can output a wide variety of wavelengths and that many organic and inorganic compounds possess strong absorption bands which can uniquely identify the unknown compound.

In an acoustically resonant photoacoustic spectroscopy apparatus, a tunable laser beam is directed into a photoacoustic resonant cell which contains a gas sample. The wavelength of the laser beam is chosen to be coincident with an infrared absorption feature of the species of gas to be detected.

The gas molecules of interest are vibrationally excited by the laser beam, and the energy absorbed by these molecules is periodically transferred to nonabsorbing surrounding gas molecules. This produces a modulated pressure rise and a resulting pressure wave which can be detected by a pressure transducer. If the laser amplitude is modulated at frequencies in the audio region, a sensitive microphone in a photoacoustic cell can be used as the pressure transducer.

However, if there are only trace amounts of gas to be detected, the resulting pressure wave will be quite small and thus difficult for the cell to detect. In such a case, detection is only possible if the cell is operated at its resonant frequency. In order to have the cell operate at its resonant frequency, the impinging pressure wave must be adjusted to compensate for varying gas composition, temperature, humidity and a variety of other conditions. Measurements of the pressure wave are made by detecting and tracking the output of the cell. To modulate the laser in this way, frequency signals from the acoustic cell must be detected and tracked. Once frequency signals from the cell are detected, the cell's frequency is employed to modulate the the amplitude of the laser beam at the cell's resonant frequency.

The signal measured by the photoacoustic detector is directly proportional to the laser power absorbed by the sample. However, these signals are very small where the unknown to be detected is present in the part per billion (ppb) range. To permit detection at the ppb level, the signal must be maximized and must be detected against a null background. That signal is maximized if the cell operates at the peak of its resonant frequency curve. That can be accomplished by modulating the amplitude of the laser beam which is incident on the cell.

The prior art discloses that the functions of acoustic frequency detection, tracking and data acquisition must be performed manually by skilled personnel, who are required to utilize expensive laboratory equipment. A phase sensitive detector and a variable frequency optical chopper have been employed in such measurements. The operational procedures consisted of searching for the unknown frequency of the photoacoustic resonant cell while simultaneously adjusting the frequency of the phase sensitive detector and the optical chopper.

These techniques are expensive and time-consuming and suited only for the laboratory. This is especially true because the prior art techniques are not suited to use in field environments where the operator must make manual adjustments to compensate for varying gas composition, temperature, humidity and other environmental conditions.

It is therefore an object of the present invention to automatically detect and track acoustic cell frequency.

SUMMARY OF THE INVENTION

A novel electronic device automatically tracks the acoustic resonance frequency of a resonant photoacoustic cell illuminated by a laser and continuously and precisely maintains the modulation frequency of the laser at that frequency, thereby permitting trace elements of a gas to be detected automatically, without need for manual intervention.

DETAILED DESCRIPTION OF THE PREFERRED EMBODIMENT

Figure 1:
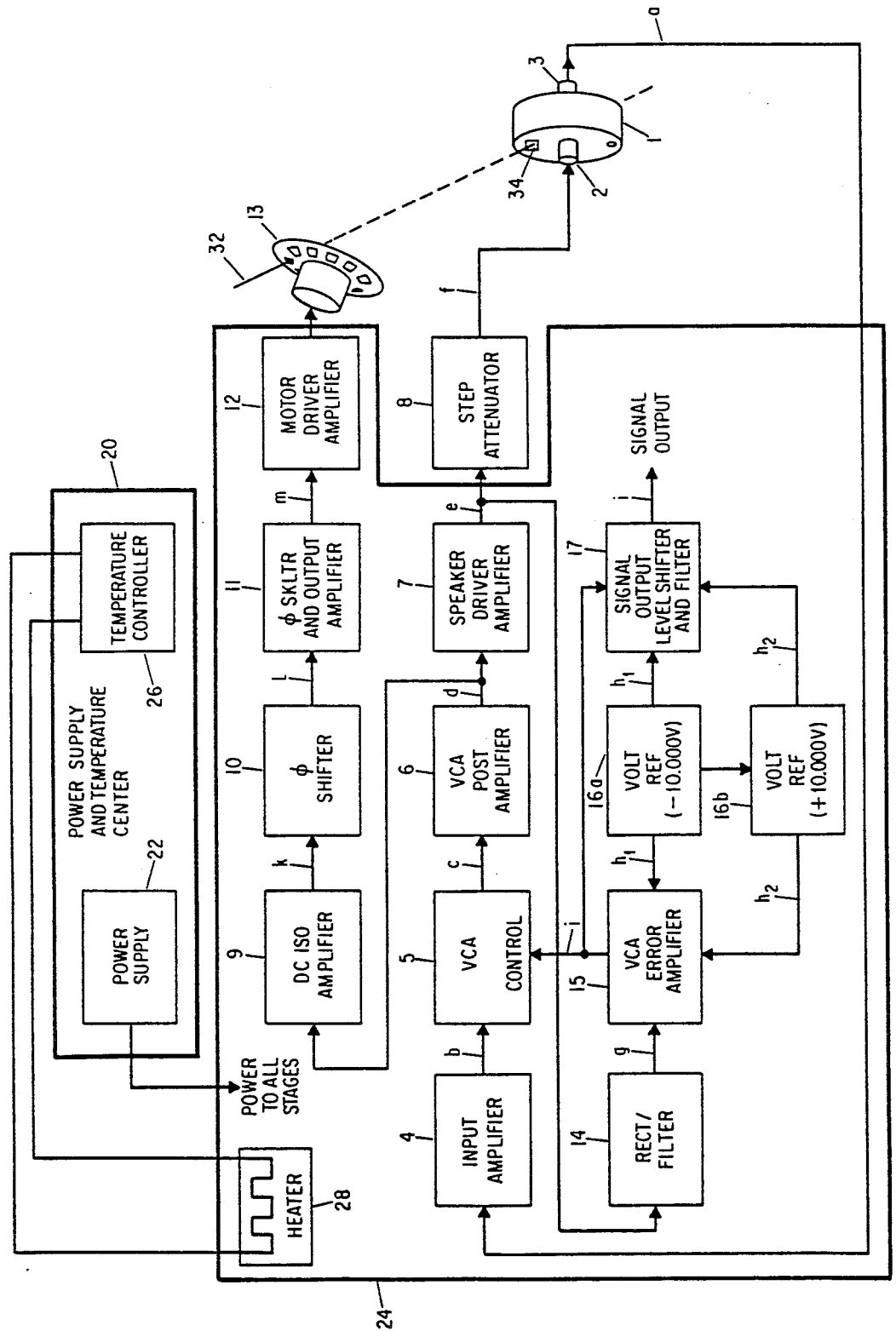
FIG. 1 is an overall system block diagram of a photoacoustic resonant system which includes frequency detection, tracking and signal acquisition functions.

Referring to an overall system block diagram shown in FIG. 1, a resonant photoacoustic cell 1 is excited into very low amplitude acoustic oscillation at its resonant frequency by means of inherent electronic system noise. This inherent electronic system noise is acoustically emitted into the resonant photoacoustic cell by a speaker 2. The photoacoustic cell oscillation is then acoustically coupled to microphone 3. The resulting voltage, which is at the photoacoustic cell's resonant frequency, is connected to input amplifier 4. The output signal from the input amplifier 4 is coupled to the voltage controlled attenuator (VCA) stage 5 and its output signal is either amplified or attenuated depending on desired resonant photoacoustic cell oscillation amplitude.

The output c of the VCA stage 5 is connected to the VCA post amplifier 6 whose output d in turn drives the speaker driver amplifier 7 and D.C. isolation amplifier 9. The speaker driver amplifier 7 provides a low output impedance for driving the step attenuator 8 and subsequently the speaker 2 and also for providing positive feedback and promoting sustained oscillation of the photoacoustic cell 1. In addition, the overall phase shift from the input signal a of input amplifier 4 through to the output f of the step attenuator 8 is essentially zero degrees, thereby promoting sustained acoustic oscillation of the photoacoustic cell 1 at its resonant frequency.

The step attenuator 8 is adjusted such that the positive feedback is just adequate to sustain acoustic cell oscillation without a photoacoustic signal present. A proportional sample of the speaker drive signal f is taken from the output of the speaker driver amplifier 7 at line e and is applied to the input of the rectifier/filter stage 14. The output of the rectifier/filter stage 14, whose output g is proportional to said acoustic oscillation amplitude, is applied to one input of the VCA error amplifier stage 15. The second input to the VCA error amplifier stage 15 is provided with a selectable reference voltage between the voltage values of reference stages 16a and 16b via connections $h_1$ and $h_2$, respectively.

The error voltage output i of the VCA error amplifier stage 15 is applied to the control input of the VCA stage 5. This error voltage is produced by continuously comparing the proportional sample of the speaker drive signal f and a selected reference voltage representative of the desired resonant photoacoustic cell oscillation amplitude. Any deviation in this error voltage is assumed to be due to amplitude changes of the output f of the step attenuator 8 and an error voltage of proper polarity and magnitude is produced such that the voltage at line f is corrected to its former selected reference value.

Thus, the output voltage of the step attenuator 8 at line f is an amplitude controlled voltage whose frequency is that of the photoacoustic resonant cell. In the case of an additional photoacoustic signal being present, the electronic system will act to correct the voltage amplitude at line f to its former value despite the fact that the additional photoacoustic signal was not produced by the electronic system. This voltage amplitude correction is affected via the control input of the VCA stage 5 and is due to a change in the voltage output i of the VCA error amplifier stage 15. Thus, a change in photoacoustic signal is translated into a change in VCA error voltage i. The VCA error voltage i is connected to the signal output level shifter and filter stage 17 where the VCA error voltage is filtered and referenced to a selectable baseline. A fixed voltage for the selectable baseline is obtained from the voltage reference stages 16a and 16b via the connections $h_i$ and $h_2$, respectively. The level shifted and filtered output signal is taken from stage 17 at line j.

The output of the D.C. isolation amplifier 9 is connected to the phase ($\phi$) shift amplifier 10 whose output 1 is shifted 180 degrees with respect to the output k of the D.C. isolation amplifier 9. The phase shift amplifier 10 output 1 is connected to a phase ($\phi$) selector and output amplifier 11 whose output m is a square wave capable of operating the chopper motor driver amplifier 12. The phase ($\phi$) shifter amplifier 10 and the phase ($\phi$) selector and output amplifier 11 compensate the electronic system for peak response with respect to the optical system employed.

The optical chopper 13 is driven by the motor driver amplifier 12. The chopper 13 is used to modulate the amplitude of laser beam 32 entering cell 1 through window 34. Slowing (at the cell's peak resonant frequency) or raising the speed of chopper 13 will amplitude modulate resonant cell 1 at a frequency other than the cell's resonance peak. In this event, system sensitivity will be decreased since signal detection will take place on a slope of the resonant cell's 1 resonance curve. FIG. 1 also shows a power supply and temperature controller 20. The power supply 22 powers all stages in the resonant acoustic frequency tracker 24 while the temperature controller 26 provides the tracker 24 with appropriate heating through a heater 28.

Figure 2A:
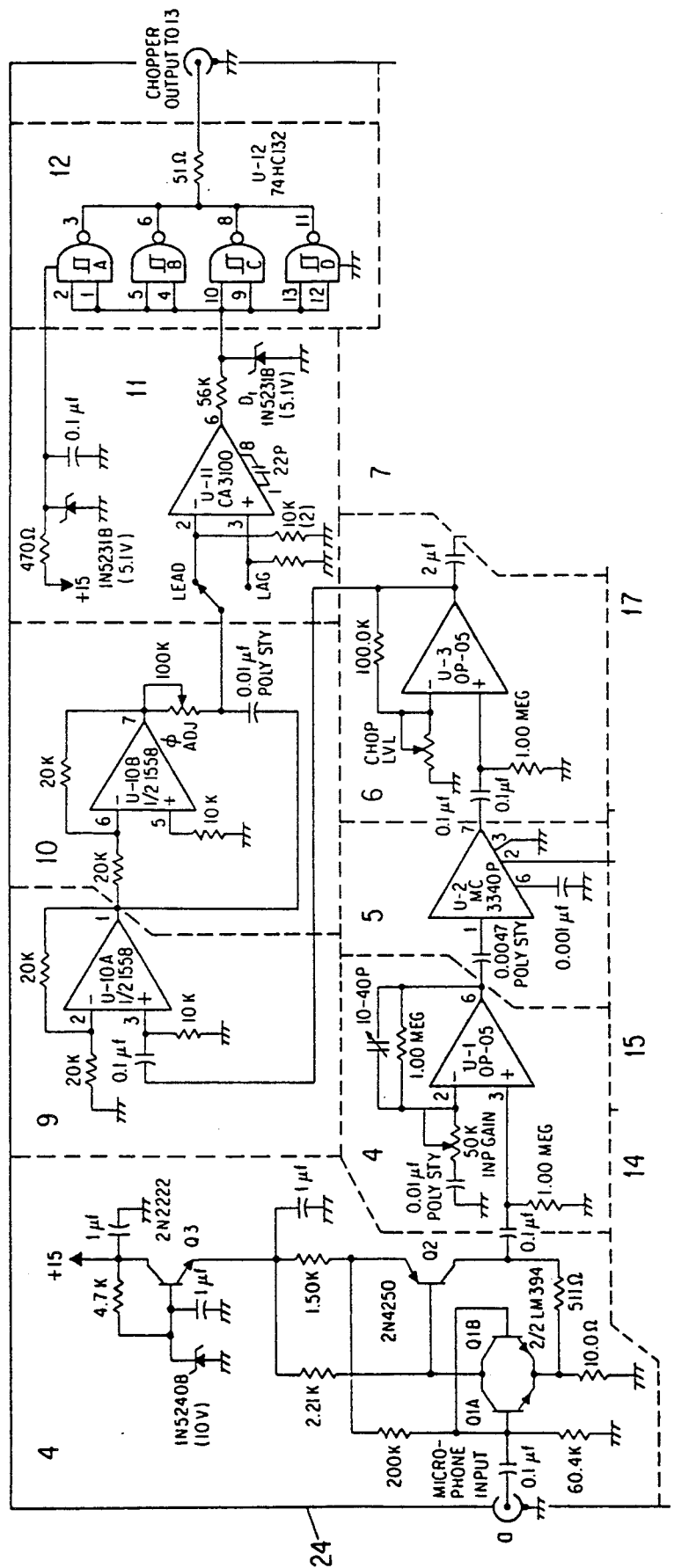
FIG. 2a and FIG. 2b illustrate the top and bottom portions of a detailed schematic diagram of the frequency detection, tracking and signal acquisition electronics.
Figure 2B:
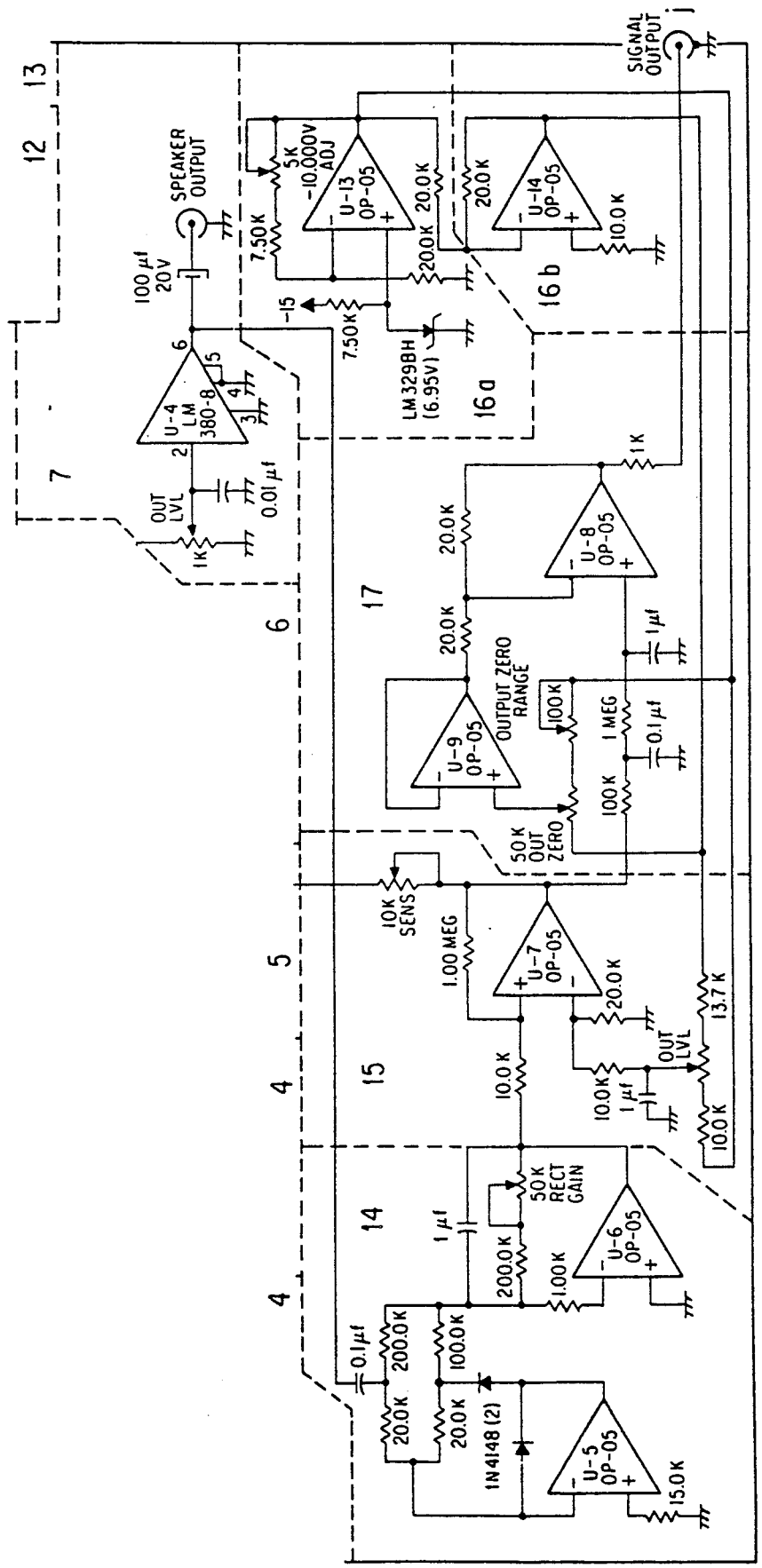

FIG. 2 is the detailed schematic diagram of the overall system block diagram, FIG. 1. Referring to FIG. 2, input amplifier 4 is formed by transistors Q1, Q2, and Q3 and operational amplifier U-1. The circuitry of input amplifier 4 is a modified version of circuitry published by National Semiconductor Corporation in the *Linear Applications Handbook* on pages AN222-3 through AN222-4. The circuit is a low noise preamplifier type of which other circuits could have produced similar results within the said electronic system.

The voltage controlled attenuator (VCA) 5 is implemented by integrated circuit U-2 and its associated components. The VCA post amplifier 6 and the speaker driver amplifier amplifier 7 are implemented by integrated circuits U-3 and U-4, respectively and their associated components.

The rectifier filter stage 14 is formed by operational amplifiers U-5 and U-6, along with their associated components. The circuit is a filtered full-wave rectifier type of circuit which was published by Howard W. Sams & Company, Inc., in *I C OP-AMP Cookbook* (second edition) by Walter G. Jung on pages 207 and 208.

The VCA error amplifier stage 15 is formed by operational amplifier U-7 and its associated components. The signal output level shifter and filter 17 is implemented via operational amplifiers U-8 and U-9. Level shifting is accomplishing within the functions of the inverting input of operational amplifier U-8. Operational amplifier U9 is employed as a reference buffer. Filter performance is provided by the network placed between the output of the VCA error amplifier and the non-inverting input of operational amplifier U-8. The system output signal is obtained from the output of U-8. The voltage reference stages 16a and 16b are formed by operational amplifiers U-13 and U-14. Operational amplifier U-13 provides an approximate gain of 1.44 in order to lower the nominal "zener" reference voltage to −10.000 v. Operational amplifier U-14 inverts the output of operational amplifier U-13 with an associated gain of one.

D.C. isolation amplifier 9 is formed by U-10A while the phase shift amplifier 10 is implemented by U-10B. Phase selection and wave shaping is performed by amplifier U-11. Operational amplifier U-11 is operated as a very high gain open loop zero crossing detector The output of U-11 is clamped and limited by Zener diode $D_1$ and applied to line driver buffer U-12. The output of U-12 is connected to the optical chopper 13.

Before operating the apparatus, the following steps are performed. The photoacoustic cell 1 is excited into very low amplitude acoustic oscillation by adjusting chopper 13 and step attenuator 8 until a minimum amplitude sustained acoustic oscillation is achieved. Flow is then stopped so as to eliminate flow noise and chopper 13 is activated when minimum sustained oscillation is achieved and is deactivated in order to prevent speed runaway. Next, the optical path is phase compensated. With a detectable sample contained within the photoacoustic cell, the laser beam is unblocked and the detected signal is maximized by adjusting phase shifter stage 10 for the amplitude of maximum output signal.

Calibration of the resonant acoustic frequency tracker is performed in order to set the dynamic range and sample concentration versus signal output transfer curve of the resonant acoustic frequency tracker. This calibration is performed against several known sample concentrations and is usually performed once upon final construction of the instrument. However, the resonant acoustic frequency tracker should be periodically checked against several known sample concentrations in order to maintain confidence or in the calibration of the apparatus.

This apparatus has been used to detect a variety of toxic compounds at low parts-per-billion (ppb) concentrations in multicomponent air samples. Also, since the apparatus monitors concentrations automatically, personnel can be afforded greater protection. For example, this apparatus was used to monitor trace levels of various hazardous compounds in ambient air sample at rocket launch sites or hazardous waste incineration sites, even in the presence of interfering gases. In one test, the presence of hydrazinc, a toxic rocket fuel, was detected at concentrations as low as 5 ppb on gas mixtures in nitrogen containing as much as 500 ppb of ethylene and ammonia and 3000 ppb methyl bromide, all of which are interfering gases.

The apparatus described above is merely illustrative of the principles of the present invention. Numerous modifications and adaptations thereof will be readily apparent to those skilled in the act without departing from the spirit and scope of the present invention.

I claim:

1. An apparatus for automatically detecting and tracking the acoustic frequency of a system, which includes a sample cell, comprising:
   (a) an oscillating means for oscillating the system at its resonant acoustic frequency;
   (b) an adjusting means for adjusting the amplitude of the system oscillation to a referenced level;
   (c) a testing means for inserting an external acoustic stimulus into the system, thereby changing the resonant frequency of the system;
   (d) an adjusting means for oscillating the system at the new resonant frequency;
   (e) a measurement means for detecting and measuring the change in the amplitude of the system oscillation;
   (f) a comparison means for the change in the amplitude of the system oscillation to known values of changes in amplitude produced by various stimuli;
   (g) whereby the type and concentration of the stimulus is determined and automatically tracked.

2. An apparatus for automatically detecting the presence of trace concentrations of an unknown gas in a gas sample cell, comprising:
   (a) means for illuminating said sample with laser light, said laser light being tuned to the absorption bands characteristic of said unknown gas;
   (b) means for detecting a resonant acoustic frequency from said cell;
   (c) means for tracking changes in said resonant acoustic frequency;
   (d) means for modulating the intensity of said laser light;
   (e) the output of said acoustic detecting means being connected to the input of said acoustic tracking means, the output of said tracking means being connected to the input of said modulating means and said modulated laser light being used to illuminate said gas sample;
   (f) whereby the identity of said unknown gas may be automatically determined by modulating the intensity of said laser light so that said cell remains at the resonant acoustic frequency of said cell.

* * * * *